United States Patent
Abdel-Rahman

[19]

[11] Patent Number: 5,804,828
[45] Date of Patent: Sep. 8, 1998

[54] METHOD AND APPARATUS FOR OPTIMIZING THE SENSITIVITY AND LINEARITY OF AN ELECTRON CAPTURE DETECTOR

[75] Inventor: Mahmoud F. Abdel-Rahman, West Grove, Pa.

[73] Assignee: Hewlett-Packard Company, Palo Alto, Calif.

[21] Appl. No.: 720,478
[22] Filed: Sep. 30, 1996
[51] Int. Cl.⁶ .................................................. G01N 27/66
[52] U.S. Cl. .......................................... 250/381; 250/379
[58] Field of Search .................................. 250/381, 379, 250/384

[56] References Cited

U.S. PATENT DOCUMENTS

| | | |
|---|---|---|
| 3,566,107 | 2/1971 | Taylor et al. . |
| 3,601,609 | 8/1971 | Yauger, Jr. ............................... 250/375 |
| 3,870,888 | 3/1975 | Lovelock ................................. 250/379 |
| 4,063,156 | 12/1977 | Patterson . |
| 4,264,817 | 4/1981 | Neukermans et al. . |
| 4,304,997 | 12/1981 | Sullivan et al. . |
| 4,651,008 | 3/1987 | Wells . |
| 4,684,807 | 8/1987 | Wells ...................................... 250/381 |
| 4,733,086 | 3/1988 | Simmonds . |
| 4,740,695 | 4/1988 | Simpson . |
| 5,479,022 | 12/1995 | Simon, Jr. ............................... 250/382 |

*Primary Examiner*—David P. Porta
*Assistant Examiner*—Richard Hanig
*Attorney, Agent, or Firm*—Mark Z. Dudley

[57] ABSTRACT

Electron capture detector for use with an effluent stream from a gas chromatograph includes an ionization cell and a sample inlet system connected to the ionization cell for providing an effluent fluid having a sample concentration therein. In the preferred constant-current, variable frequency mode of operation, a cell current is measured and compared to the reference current. The pulse rate is then adjusted to maintain a constant cell current. The pulse rate is converted to a voltage, processed according to a novel linearization formula, and recorded. The ionization cell includes a radioactive ionization source and the ionization cell defines an optimized cell volume in which the electron capture reaction is forced to occur according to a concentration mode of operation. Improved sensitivity in the electron capture detector may be achieved by restricting the effective radioactivity in the ionization cell to be in the range of 0.5 to 3 milliCuries, and preferably in the range of 1 to 2 milliCuries. The ionization cell volume is substantially reduced while the aforementioned effective level of radioactivity is nonetheless maintained. Linearization of the electron capture detector is obtained by overcoming and/or compensating for several sources of nonlinearity by: (1) forcing the detector to operate in only the concentration mode of operation, and (2) processing the signal derived from the detector response so as to compensate for a heretofore unrealized logarithmic decay of the response factor at higher sample rates.

8 Claims, 7 Drawing Sheets

METHOD AND APPARATUS FOR OPTIMIZING THE SENSITIVITY AND LINEARITY OF AN ELECTRON CAPTURE DETECTOR

FIELD OF THE INVENTION

This invention relates generally to ionization detectors and more particularly to an electron capture type of detector for use in detecting the constituents of a sample eluted from a chromatograph.

BACKGROUND OF THE INVENTION

Electron capture detectors for gas chromatography are well known in the art. For example, a review of such detectors is contained in an article entitled "Electron Capture Detectors for GC", by Debra Noble, *Analytical Chemistry*, Jul. 1, 1995, pages 439A–442A. The electron capture detector (ECD) is extremely sensitive to chain molecules such as alkyl halides, but is relatively insensitive to hydrocarbons, alcohols, ketones, etc. This type of detector features high sensitivity and high selectivity towards electrophilic compounds and is widely used for detecting trace amounts of pesticides in biological systems and in food products. Such compounds typically contain halogens which combine with free electrons created in an ionization cell in the detector. The resulting decrease in free electrons in the ionization cell is monitored and used as an indication of the concentration of the compounds in a sample.

The response of the typical electron capture detector has been observed to be dependant upon many variables, such as the molecular composition of the sample and its concentration, the cleanliness and temperature of the detector cell, and the flow rates of the make-up gas and effluent. However, the behavior of the electron capture detector with regard many of these variables is not completely understood.

During its early use the electron capture detector was operated in the direct current (DC) or the fixed frequency (FF) pulsed modes of operation where the change in current (I) was taken as the response. Detectors operated in either of these two modes yielded linear calibration curves only over the initial 10% of the entire response range. In 1967 Wentworth and Chen (*J. Gas Chromatogr.* 5 (1967), p. 170) showed that if the analytical response in the fixed frequency mode was taken as $(1°-I)I$, where $1°$ is the measured standing current in the absence of sample and I is the cell current measured continuously during the chromatogram, that linear calibration curves could be obtained up to and exceeding 90% of detector saturation. A practical limitation of this mode of signal processing is its requirement for unusually clean chromatographic conditions so that a high standing current with long pulse periods can be achieved. In 1971 Maggs et al. (Anal. Chem. 43 (1971) p. 1966) proposed operating the electron capture detector in the frequency modulated, or "constant current" (CC) mode of operation. In this mode, a feedback network causes the magnitude of the measured current to be constant and equal to a preselected reference value by control of the pulsing frequency. As an electron capturing compound passes through the cell the frequency of pulsing increases by an amount required to keep the current constant. The analytical response is taken as the increase in frequency of pulsing.

Calibration curves are often made, whereby the detector response factor (i.e., the detector response divided by sample concentration) is made constant within a few percent over three orders of magnitude of dynamic range. As a result, the electron capture detector is now widely used in gas chromatography, often permitting sensitivity to compounds present in quantities as low as several femtograms.

However, under apparently unvarying conditions, the constant current electron capture detecton can exhibit symptoms of a nonlinear and unpredictable relationship between the measured response and analyte concentration. As shown in FIG. 1 (reproduced from J. J. Sullivan, C. A. Burgett, NON-LINEARITY IN CONSTANT CURRENT ELECTRON CAPTURE DETECTION, *Chromatographia*, Vol. 8, No. 4, April 1975), the magnitude of the non-linearity can such that the response at a low sample concentration is less than half of the response at high sample concentration. Nonlinear responses of this type have been previously described (cf. Sullivan & Burgett, supra; Lovelock, *J. Chromatgr.* 99, (1974),3, Lovelock & Watson, *J. Chromatgr,* 158, (1978), 123; Grimsrud & Knighton, *Anal. Chem.* 54, (1982), 565).

Hence, quantitation is difficult because the electron capture detector is now generally expected to provide nonlinear responses to those compounds (such as highly halogenated hydrocarbons) for which it is most sensitive. The lack of linearity to this important group of compounds has been attributed not to instrumental deficiencies but to, e.g., aspects of the alteration of the sample concentration within the detector by the electron attachment process itself.

Knighton & Grimsrud, in *Analytical Chemistry* 55, (1983), pp. 713–718 explain the response of the electron capture detector to strongly responding compounds as follows: At low sample concentrations a significant fraction of the sample is ionized by the electron capture reaction because the electron capture rate constant ($k_1$) and the average electron density ($e^-$) are both large. Under this low sample concentration condition, an approximately linear response is observed as long as the electron population remains high and relatively constant, causing the same fraction of analyte molecules to be reacted over this limited sample concentration range. However, as the concentration of the sample increases, a smaller population of electrons consumes a successively smaller fraction of the analyte entering the cell. The detector response is said to be directly proportional to the instantaneous concentration of the analyte within the detector, and the response is therefore observed to lack a linear relationship to the analyte concentration entering the cell over the entire dynamic range of the detector. The authors describe the use of signal processing as an approach that is said to offer improved linearity for strongly responding compounds using a detector of any size or design and operated at conventional flow rates. The authors describe a constant current mode of control that is operated with an extended definition of the processed response; an improvement is said to occur because the alteration of analyte concentration by the attachment of electrons is accounted for and incorporated into the response function. The disclosed definition employs linear calibration curves for strongly electron attaching molecules over the dynamic range of the instrument, wherein the response of the detector to strongly responding compounds is taken according to the function:

$$(f-f_0)(H+f)/f$$

where $f$ is the instantaneous frequency of pulsing, $f_0$ is the baseline (or analyte-free) frequency, and H is an experimentally-determined constant. However, the application of such a calibration scheme is not as effective with other types of electron-capturing compounds. A further disadvantage of this approach is that the calibration curves tend to shift in response to changes in the detector background noise, and the calibration curves are thus less than fully effective.

Practitioners in the art have observed that the radioactive ionization source creates free electrons from relatively few beta particles. It is also generally held that a greater number of free electrons in the ionization cell will enable a smaller minimum detectable quantity (mdq) of the sample to be achieved. Another observation is that the emitted beta particles have a relatively long range. Accordingly, one conventional design approaches to enlarge the volume of the ionization cell, to a volume on the order of a 1.0 to 1.5 milliliters, to increase the effective level of radioactivity, thus enabling greater free electron production, and to avoid undesirable cross-section effects. However, such a large volume becomes a serious drawback as the detector is not suited for efficient use with capillary columns that elute small gas flows and therefore require a smaller ionization cell volume. Increasing the level of effective radioactivity also engenders significant shot noise, which limits the minimum detectable quantity of the sample.

A contrary approach to this problem is to make the ionization cell volume very small, or to make the carrier flow rate very fast, such that the residence time of the analyte in the ionization cell is then very short and ionization of the sample by the electron capture reaction is reduced. The reduced volume approach has been demonstrated by Patterson (in *J. Chromatgr.* 134 (1977), 25), where the active volume of a small cell was made effectively smaller by use of a displaced coaxial anode. However, when the ionization cell volume of an electron capture detector is reduced, more beta particles are lost at the cell walls instead of ionizing the make-up gas and less interior surface area is available for locating the radioactive source in the cell; as a result, there is a reduction in the number of thermal free electrons available to interact with the chemical analyte. Hence, in this approach, there is a practical limit to reducing the ionization cell volume. At best, the detector response to strongly responding compounds is only partially improved, whereas the sensitivity of the electron capture detector to weakly and moderately responding compounds is proportionately reduced.

Accordingly, there remains a need for an improved design approach and methodology for construction and operation of an electron capture detector, wherein the aforementioned conflicting conditions and limits can not only be better understood, but also optimized to one's advantage, such that the sensitivity and linearity of the electron capture detector is optimized.

SUMMARY OF THE INVENTION

This invention relates generally to an electron capture detector having improved detector response, and in particular to a method and apparatus for improving both the linearity and sensitivity of the detector response exhibited by an electron capture detector used in a high resolution gas chromatograph. As described herein, the "detector response factor" is considered to be the detector response per unit of sample that is subject to detection; the "cell volume" is considered to be the volume defined by an ionization cell in an electron capture detector; and the "effective radioactivity" is considered to be the level of radioactivity induced in an ionization cell volume due to the presence of a radioactive ionization source.

In the preferred embodiment of the present invention, the above and other features are achieved by providing an electron capture detector having an ionization cell and a sample inlet system connected to the ionization cell for providing a fluid mixture having an electron-capturing species subject to detection in the ionization cell. The ionization cell includes a radioactive ionization source, preferably in the form of a radioactive foil applied to the cell interior wall. The ionization cell defines an optimum cell volume and is subject to an optimum effective level of radioactivity such that the electron capture reaction is forced to occur according to a concentration mode of operation.

In the preferred constant-current, variable frequency mode of operation, a cell current is measured and compared to the reference current. The pulse rate is then adjusted to maintain a constant cell current. When a sample compound that captures electrons is present in the ionization cell, the pulse rate varies. The pulse rate is converted to a voltage, which is processed by an interface according to a novel linearizing formula, and provided as the detector output signal for subsequent analysis and/or recording.

Thus, in contrast with the prior art, wherein it is generally held that a greater effective radioactivity, and hence a larger the number of free electrons available, enables a smaller mdq, I have determined that there is an optimum level of effective radioactivity at which the lowest minimum detectable level may be achieved. Improved sensitivity in an electron capture detector may be achieved according to the present invention by restricting the level of effective radioactivity in the ionization cell to the range of 0.5 to 3 milliCuries, and preferably in the range of 1 to 2 milliCuries.

In another departure from the prior art, I have found that the ionization cell volume can be substantially reduced while the aforementioned effective level of radioactivity is maintained. The preferred level of effective radioactivity is best effected by reducing the cell volume below that of the ionization cell volume in conventional electron capture detector. For example, the optimum cell volume was found to be in the range of 100–150 microliters ($\mu l$) for an electron capture detector having a $N_{63}$ radioactive source and operating in the range of 200–400 degrees centigrade (C.) at atmospheric pressure.

I have further determined that a significant contributor to the nonlinearity in prior art electron capture detectors is due largely to conventional operation across two modes of detection. In a first mode of operation, occurring at low sample concentrations, most of the sample molecules are found to capture substantially all of the free electrons (in what is termed the coulometric mode of detection). In a second mode of operation, occurring at high sample concentrations, the sample capture rate may be observed to be a function of the free electron concentration and the sample concentration (in what is termed the concentration mode of detection). During the transition between these first and second modes of operation, occurring at moderate sample concentrations, the detector operates between the coulometric and the concentration modes. I have determined that the detector response factor exhibits disadvantageous nonlinearity as the detector operation changes between these two modes of detection. This contributor to nonlinearity in the detector response typically arises when varying concentrations of differing sample compounds are analyzed. For example, at higher sample concentrations, certain compounds have been found to cause a response factor that is several times higher-than the response factor exhibited at lower sample concentrations of the same compound. Other compounds may cause an opposite effect, that is, a much smaller response factor is exhibited at high sample concentrations and a large response factor at low sample concentrations. Hence, in the transition between coulometrie and concentration modes of operation, the detector response factor for a given sample will vary considerably.

Detector operation in the concentration mode may be shown to occur wherein the number of free electrons at steady state is determined by the relationship:

$$C = k_1(e)(B/u)$$

Where:
C=rate of capture, electrons/sec
B=rate of analyte introduction, molecules/sec
U=flow rate through the cell, milliliters/sec
e=number of free electrons
$k_1$=rate constant of electron capture This relationship, when solved with the prior art assumption that $k_1$ is constant, has heretofore been expected to show a linear detector response (e.g., wherein detector output frequency is proportional to B).

In another departure from the prior art, I have found that in actuality, $k_1$ is not constant. At higher sample concentrations, the number of free electrons become much smaller than the number of sample molecules. I have thus observed that a substantially logarithmic decay of the response factor occurs during the concentration mode, and in particular during ionization conditions wherein the number of uncaptured free electrons is much less than the number of sample molecules present in the detector ionization cell. When this happens, an increase in the sample concentration does not cause a proportionate increase in the number of free electrons. Hence, I have found that k, should be considered to decline in logarithmic fashion as the sample concentration increases.

Linearization of the electron capture detector according to the present invention may be obtained by overcoming and/or compensating for some or all the aforementioned sources of nonlinearity. This is achieved by one or both of the following: (1) forcing the detector to operate in only the concentration mode of operation, and (2) processing the signal derived from the detector response so as to compensate for the logarithmic decay of the response factor at higher sample rates.

Hence, in one aspect of the invention, linearization is achieved by providing an optimum level of effective radioactivity level in the ionization cell of the detector, thus restricting the detector operation to the concentration mode. Reducing the ionization cell volume to an optimum volume also forces the recombination constant $k_d$ to become significantly larger, thus also forcing the detector into the concentration mode. An optimum ionization cell volume in the range of approximately 100–150 microliters ($\mu l$) provides a maximum effective radioactivity of approximately 1–2 milliCuries and a $k_d$ sufficiently large to cause the detector to operate in the concentration mode.

In another aspect of the present invention, I have found by empirical determination that this logarithmic decline in $k_1$ can be compensated by altering the detector signal derived from the detector response according to a linearizing formula:

$$f_{(lin)} = f[1 + (f/f_{(dec)})]^{pwr}$$

Where:
$f_{(lin)}$=linearized output frequency of the electron capture detector
$f$=non-linearized output frequency of the electron capture detector
$f_{(dec)}$=detector frequency at which $k_1$ begins its observed decline pwr=power of the decline in $k_1$ In a preferred embodiment of the invention, implementation of this linearizing formula can be accomplished via signal processing of the detector signal by way of a linearizing section in a detector output signal interface. The preferred compensation thus may be implemented in discrete electronic circuitry (i.e., in hardware), firmware, or software.

Such linearization of the output response to account for the non-linearity of the rate constant $k_1$ may be applied to any ionization detector operating according to the above-described concentration mode of operation. This include helium ionization detector, argon ionization detector whether radioactive or non-radioactive types.

ADVANTAGES OF THE INVENTION

An electron capture detector constructed according to the present invention has been observed to operate with improved sensitivity and linearity over a heretofore unrealized dynamic range (i.e., approximately six decades of sample concentration). The electron capture detector has demonstrated this outstanding sensitivity and linearity over a wide range of gas flow rates and detector temperatures. Neither makeup gas type, nor moderate levels of contamination, have been found to degrade the detector linearity. Analytical laboratories that heretofore have found difficulty in meeting the linearity requirements for government-mandated analysis of certain compounds, e.g., those found in pesticide analysis, will be able to use the teachings of this invention to operate an electron capture detector that meets the linearity requirement with great ease.

As the linear dynamic range of this detector extends for six decades of sample concentrations, analytical applications requiring a wide range of sample concentrations are now feasible. For example, applications that heretofore required preparatory steps for sample dilution or sample concentration may be accomplished without the need for such steps.

An electron capture detector constructed according to the present invention has also been observed to be less sensitive to contamination and thus requires less frequent cleaning. These advantages enabling the electron capture detector to be operated longer, without interruption, for significant increase in sample throughput and operator productivity. In contrast to prior art detectors, wherein linearity is seen to vary with the factors such as the cleanliness of detector gas or make-up gas, or the extent of column bleed, and which are subject to frequent re-calibration (a tedious task that adversely impacts productivity), linearity in the preferred embodiments is far less dependent on the aforementioned factors. An initial calibration will be effective for a much longer period.

An electron capture detector constructed according to the present invention utilizes a smaller ionization cell volume than typically found in the prior art. Narrower chromatographic peaks are thereby detectable, and shorter chromatographic runs and high sample throughput can then be achieved.

The teachings of this invention apply to any detector operating on ionization of a fluid mixture, such as a helium ionization detector, argon ionization detector, and other electron capture detectors having either radioactive or non-radioactive electron sources.

DETAILED DESCRIPTION OF THE PREFERRED EMBODIMENTS

Figure 1:
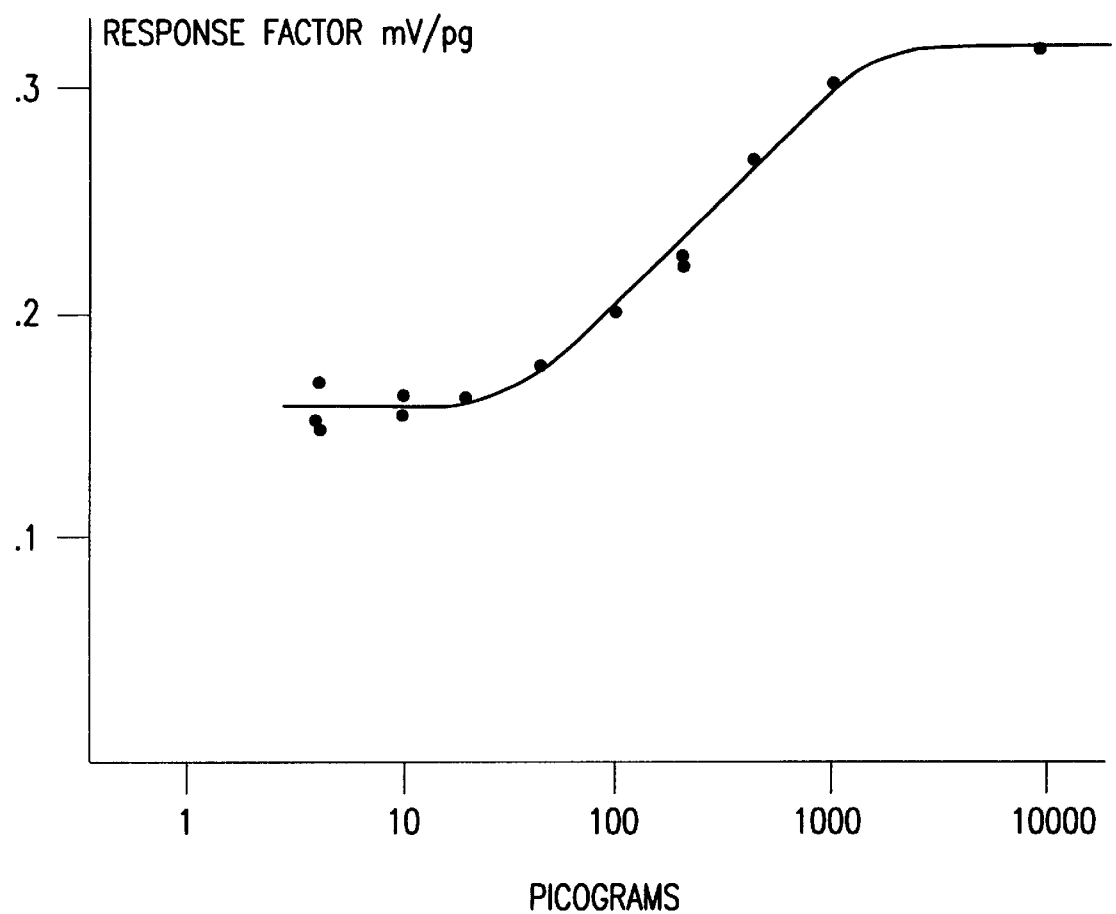
FIG. 1 is a graphical representation of the response factor nonlinearity exhibited by a prior art electron capture detector.

The apparatus and methods of the present invention may be employed in particular to improve the detection of an analyte that may be present in a variety of fluids. Gases are the preferred fluids according to the practice of the present invention, and therefore the following description of the invention will include a description of the arrangement, construction, and operation of a novel electron capture detector in a gas chromatographic analytical system (hereinafter, a chromatograph).

Embodiments of the invention described herein are contemplated for use as a temperature-controlled, constant-current, pulse-modulated electron capture detector in a gas chromatograph. The basis for operation of the contemplated detector with respect to a chromatograph may be generally understood as follows. In a chromatographic separation of a given sample compound, a sample is injected with a pressurized carrier gas into a separation column and the column effluent is directed as a fluid stream into the electron capture detector. One or more pneumatic manifold assemblies are envisioned, each of which serves in part to control and redirect a plurality of gas flows, including the carrier gas and a plurality of detector gases of appropriate types such as air, hydrogen, and make-up gas. Accordingly, the pneumatic manifold may be operated to effect a modulation of any of the aforementioned gas flows, and in particular to supply modulated purge gas flow and make-up gas flow to the electron capture detector described hereinbelow. Aspects of such fluid supply in the embodiments illustrated in FIGS. 2 et seq. is preferably provided via electronic pneumatic control (EPC). For further details of electronic pneumatic control techniques, one may consult, for example, Klein, et al., U.S. Pat. No. 4,994,096 and U.S. Pat. No. 5,108,466, the disclosures of which are incorporated herein by reference.

In particular, however, the embodiments of the invention described herein are contemplated as being constructed and operated according to heretofore unrealized aspects of optimal design, construction, and operation of an electron capture detector; the theoretical basis for these aspects will first be presented in a section entitled "Theory of the Invention". The following section, entitled "Construction and Operation of an electron capture detector in a GC System", will describe the construction and operation of the preferred embodiment of the contemplated electron capture detector with respect to a chromatograph.

1.0 Theory of the Invention
1.1 Introduction
1.1.1 Electron Capture Detector Rate Equation
When equilibrium is reached in the electron capture detector ionization cell, the rate of generation of free electrons will equal the rate of electron removal.

$$A = e \cdot k_d + C \qquad \text{eqn.1}$$

Where:
A=rate of electron generation by beta particle ionization (electrons sec$^{-1}$)
C=rate of electron capture by the chemical analyte (electrons sec$^{-1}$)
e=number of free electrons found in the cell at any time (electrons)
$k_d$=rate constant of free electrons recombination with the positive ions. (sec$^{-1}$)
This constant also includes electrons lost by other processes, particularly those lost to cell walls
1.1.2 Coulometric Mode of Electron Capture Detection
At very low analyte concentrations, there is relative abundance of free electrons and each and every analyte molecule captures the maximum number of electrons possible. This is the coulometric mode of detection. Therefore, we can write:

$$C = n \cdot B$$

Where:
n=the maximum number of electrons that can be captured by one analyte molecule. I observed that for standard pesticides samples, n takes a value between 1 and 10 depending on the pesticide molecular structure.
B=rate of introduction of the analyte into the ionization cell (molecules sec$^{-1}$)
Substituting from eqn.2 in eqn. 1, we get the coulometric mode rate equation:

$$A = e \cdot k_d + n \cdot B \qquad \text{eqn.3}$$

1.1.3 Concentration Mode of Electron Capture Detection
In the ionization cell, free electrons and analyte concentrations can be expressed as:

$$\text{electrons concentration} = \frac{e}{V} \text{ electrons} \cdot \text{cm}^{-3} \qquad \text{eqn.4}$$

$$\text{analyte concentration} = \frac{B}{U} \text{ molecules} \cdot \text{cm}^{-3} \qquad \text{eqn.5}$$

Where:
V=ionization cell volume (cm$^3$)
U=gas flow rate through the ionization cell (cm$^3$ sec$^{-1}$)
When the concentration of the analyte molecules is greater than the that of free electrons, the rate of electron capture "C" becomes proportional to the free electrons concentration, the active analyte concentration and the cell volume. Because of the rarity of electrons, most molecules will only capture one electron and the capture rate "C" is therefore independent of the analytes "n" number. The constant of proportionality $k_1$ is analyte dependent. Therefore we can write:

$$C = k_1 \cdot \frac{e}{V} \cdot \frac{B}{U} \cdot V, \text{ or: } C = k_1 \cdot e \cdot \frac{B}{U} \qquad \text{eqn.6}$$

Substituting eqn.6 in eqn. 1, we get the concentration mode rate equation:

$$A = e \cdot k_d + k_1 \cdot e \cdot \frac{B}{U} \qquad \text{eqn.7}$$

1.1.4 Response Factors in the Constant Current Pulsed Design

In the constant current pulsed design, the anode is pulsed with a narrow positive electrical pulse to momentarily collect any available free electrons in the cell. The pulse frequency is varied to achieve an average net current of fixed magnitude. Thus, as more and more electron capturing analyte is introduced into the cell, the pulse frequency increases to account for the reduction in the electrons available for collection. In this design, the pulsing frequency is the detector output signal.

To maintain a constant current collection, the following equation applies:

$$e(B) \cdot f(B) = e_0 \cdot f_0 \qquad \text{eqn. 8}$$

Where:
e(B)=number of free electrons available for collection as a function of analyte introduction rate "B"
f(B)=pulse frequency as a function of "B" (Hz)
$e_0 = e(0)$ = value of e(B=0)
$f_0 = f(0)$ = value of f(B=0) (Hz)
Making C=0 in eqn. 1, we get:

$$A = e_0 \cdot k_d + 0, \text{ or: } e_0 = \frac{A}{k_d} \qquad \text{eqn.9}$$

The detector response factor as a function of the analyte introduction rate B can be expressed as follows:

$$R(B) = \frac{f(B) - f(0)}{B} \text{ (Hz molecule}^{-1}\text{ sec)} \qquad \text{eqn.10}$$

Substituting from eqn.8 in eqn.9, we get:

$$R(B) = \frac{e_0 \cdot f_0}{B} \cdot \left( \frac{1}{e(B)} - \frac{1}{e(0)} \right) \text{ (Hz molecule}^{-1}\text{ sec)} \qquad \text{eqn.11}$$

1.1.5 Electron Capture Detector Response Factor in the Coulometric Mode

Substituting from eqn.3 in eqn.11, we can obtain R(B) for the coulometric mode:

$$R(B)_{Coul.} = \frac{f_0 \cdot n}{A - n \cdot B} \text{ (Hz molecule}^{-1}\text{ sec)} \qquad \text{eqn.12}$$

For the prior art detectors operating at an effective radioactivity of 15 milliCurie, n.B<<A and we can approximate eqn.12 to:

$$R(B)_{Coul.} = \frac{f_0 \cdot n}{A} \text{ (Hz molecule}^{-1}\text{ sec)} \qquad \text{eqn.13}$$

Eqn. 12 shows that in the prior art detectors, the response factors for different compounds are quantum in nature (because n is an integer>1).

1.1.6 Electron Capture Detector Response Factor in the Concentration Mode

Substituting from eqn.7 in eqn. 10, we can obtain R(B) for the concentration mode:

$$R(B)_{Conc.} = \frac{f_0 \cdot k_1}{k_d \cdot U} \text{ (Hz molecule}^{-1}\text{ sec)} \qquad \text{eqn.14}$$

Note that with the conventional assumption that $k_1$ is constant, the $R(B)_{Conc.}$ is expected to be constant and the electron capture detector response in the concentration mode is thought of as linear. However, this assumption will be shown below to be incorrect.

1.1.7 Electron Capture Detector Non-linearity Due to Transitions From One Mode of Detection to Another This is the major cause of non-linearity in the conventional 15 milliCurie detectors. The response factor in the coulometric mode $R(B)_{Coul.}$ and that of the concentration mode $R(B)_{Conc.}$ are different. As a result, prior art electron capture detectors experience dramatic change of response factor as the analyte amount increases from low levels to high levels. This transition extends over about two orders of magnitude (1 picogram (pg) to 100 pg of analyte injections) which lies in the middle part of the dynamic range. A good measure of this non-linearity is the ratio of the two response factors. Substituting from eqn. 13 and eqn. 14, we get:

$$NL_{factor} = \frac{R(B)_{Conc.}}{R(B)_{Coul.}} \qquad \text{eqn.15}$$

$$= \frac{A \cdot k_1}{n \cdot k_d \cdot U} \text{ (Hz molecule}^{-1}\text{ sec)}$$

Substituting from eqn.2, we get:

$$NL_{factor} = \frac{e_0 \cdot k_1}{n \cdot U} \text{ (Hz molecule}^{-1}\text{ sec)} \qquad \text{eqn.16}$$

For a linear response over the whole dynamic range, this factor must be equal to unity. In the conventional 15 milliCurie/1500 microliter detector and for highly capturing analytes and moderate flow rates, this factor is greater than 1. For analytes with low $k_1$, $NL_{factor}$ is less than 1. Therefore, an attempt to change the flow rate U to linearize any one analyte may cause other analytes to detected in a more non-linear fashion. Furthermore, creating calibration curves for different analytes is tedious. (Detector contamination acts like a background analyte and moves the analytes under test up and down the transition portion of the response factor curve, thus changing the response unpredictably.)

The foregoing analysis clearly indicates that a detector operable in both modes of detection is, in practical terms, impossible to linearize.

1.1.8 Conclusion of the Previous Discussion

Based on the previous analysis, one can conclude that to design a substantially more linear electron capture detector, the mode of detection transition region has to be avoided. This means that a linear electron capture detector design is best operated in one mode of detection, and as will be shown below, preferably in the concentration mode over its whole dynamic range.

A detector with any value of $e_0$ will theoretically work in both modes, but an important aspect is the practical limits of sample size. The lower limit of the sample size of course is the MDL. By designing a detector with a small value of $e_0$ such that its MDL in molecules is about the same order of magnitude as the $e_0$, we can achieve a detector that operates only in the concentration mode. On the other hand, by designing a detector with $e_0$ much greater than the MDL, we achieve a detector that can operate only in the coulometric mode.

Which of the two designs is more sensitive (i.e., offers lower MDL)?. How is detector sensitivity (MDL) affected by the amount of radioactivity and other detector parameters such as the gas flow rate, the analyte k1 and the detector size?.

In order to answer these very important questions, I developed a mathematical model that describes the electron capture detector response in the two modes of detection as well as the transition period. Noise formulas for the electron capture detector predict a far greater noise level than empirically measured in conventional detectors. So, a correct formula for electron capture detector noise has to be derived.

Using the response model and the noise model, one can derive a mathematical model for MDL as a function of detector parameters.

1.2. Universal Equation for the Electron Capture Detector Response

The word "universal" means the electron capture detector response is characterized over both modes of detection as well as the transitional area. In other words, it describes the response over the whole dynamic range of the detector. Let us define "$M_e$" to be the effective concentration of analyte molecules ready to capture free electrons. "$M_e$" can be expressed as:

$$M_e = \frac{B - \frac{C}{n}}{U} \quad \text{molecules} \cdot \text{cm}^{-3} \qquad \text{eqn.17}$$

The rate of electron capture by the analyte "C" is proportional to the free electrons concentration "e/V", the analyte-free molecules concentration "$M_e$", and the cell volume. Therefore, we can write:

$$C = k_1 \cdot \frac{e}{V} \cdot \frac{B - \frac{C}{n}}{U} \cdot V \qquad \text{eqn.18}$$

$$C = k_1 \cdot e \cdot \frac{B - \frac{C}{n}}{U}$$

Solving eqn. 18 for "C", we get:

$$C = \frac{\frac{e \cdot k_1}{U} \cdot B}{1 + \frac{e \cdot k_1}{n \cdot U}} \qquad \text{eqn.19}$$

Let us assume that: $e \cdot k_1 \gg n \cdot U$. Then, eqn.19 can be approximated to:

$$C \approx n \cdot B \qquad \text{eqn.20}$$

Eqn.20 is similar to eqn.2 which describes the coulometric mode of detection. Let us assume that: $e \cdot k_1 \ll n \cdot U$. Then, eqn.19 can be approximated to:

$$C \approx k_1 \cdot e \cdot \frac{B}{U} \qquad \text{eqn.21}$$

Eqn.21 is similar to eqn.6 which describes the concentration mode of detection. Note that in eqn.19, as B gets larger, e gets smaller and $e \cdot k_1/n \cdot U$ becomes smaller, thus moving the detector towards the concentration mode. It is important to observe that to design a detector that operates only in the concentration mode, the condition needed is:

$$\frac{e_{mdl} \cdot k_1}{n \cdot U} \ll 1 \qquad \text{eqn.22}$$

Where:
$e_{mdl}$=the value of e when the B=MDL.
Since in practical detector design $e_{mdl}$ is approximately equal to $e_0$, eqn. 22 becomes:

$$\frac{e_0 \cdot k_1}{n \cdot U} \ll 1 \qquad \text{eqn.22.1}$$

Substituting from eqn. 19 into eqn. 1 we get the desired universal rate equation:

$$A = e \cdot k_d + \frac{\frac{e \cdot k_1}{U} \cdot B}{1 + \frac{e \cdot k_1}{n \cdot U}} \qquad \text{eqn.23}$$

By solving eqn. 23 for e(B) and substituting in eqn. 11 using a mathematics computation program, such as Mathematica, plots of the response factor for different parameters were obtained.

1.3. Shot Noise in the Electron Capture Detector

Shot noise of dc current is described by the equation:

$$N_{sh} = \sqrt{2 \cdot q \cdot I_{dc} \cdot \Delta f} \quad \text{amps(rms)} \qquad \text{eqn.24}$$

$$= q \cdot \sqrt{2 \cdot \frac{I_{dc}}{q} \cdot \Delta f} \quad \text{amps(rms)}$$

$$= \sqrt{2 \cdot \frac{I_{dc}}{q} \cdot \Delta f} \quad \text{electrons sec}^{-1}\text{(rms)}$$

Equation 24 applies for the case when each electron arrives at random. For the case when bursts of N electrons are generated, eqn. 24 becomes:

$$N_{sh} = \sqrt{2 \cdot N \cdot \frac{I_{dc}}{q} \cdot \Delta f} \quad \text{electrons sec}^{-1}\text{(rms)} \qquad \text{eqn.25}$$

For the case of the electron capture detector, three shot noise mechanisms exist (also refer to eqn.1):

1. The shot noise in the "A" term due to electron generation by beta particles.
2. The shot noise in the "$k_d \cdot e$" term due to the recombination of free electrons with positive ions and the cell walls.
3. The shot noise in the "C" term due to the analyte(s) capturing free electrons.

The value of N for the recombination and the capture processes is equal to 1. While N is>25 for practical electron capture detectors. This leads us to the conclusion that the shot noise of the electron capture detector is mainly due to the electron generation process. Therefore, we can write:

$$A_{sh} = \sqrt{2 \cdot N \cdot A \cdot \Delta f} \quad \text{electrons/sec(rms)} \qquad \text{eqn.26}$$

Where:
$A_{sh}$=shot noise in A.
Since the actual electron capture detector signal is derived from successive collections of "e", we can calculate the noise content of $e_0$ as "$N_{eo}$".

$$A = k_d \cdot e_0 \text{ or } e_0 = \frac{A}{k_d} \qquad \text{eqn.27}$$

$$\therefore N_{e0} = \frac{A_{sh}}{k_d} = \frac{\sqrt{2 N A \Delta f}}{k_d} \quad \text{electrons(rms)}$$

Let us assume that the peak to peak noise is six times the root-mean-square (rms) of the noise value, therefore:

$$N_{p-p} = 6 N_{e0} = 6 \cdot \frac{\sqrt{2 N A \Delta f}}{k_d} \quad \text{electrons(rms)} \qquad \text{eqn.28}$$

This is the true expression of electron capture detector noise. Experimentation has shown it to agree with empirical noise measurements. In contrast to the teachings in the prior art, the electron capture detector noise must be calculated for "e" . . . and not for the cell current. Calculating noise for the cell current, or for the rate of free electron production "A", gives an erroneously large values.

1.4. Derivation of MDL in electron capture detector

Let us assume that the minimum detectable level of an analyte $B_{mdl}$ is the value of B that causes a reduction in $e_0$ equal to the peak to peak noise $N_{p-p}$. Thus, we can write:

$$e_0 - e_{mdl} = N_{p-p}$$

Where:

$$e_{mdl} = e(B_{mdl})$$

Substituting for Np-p from eqn.28 we get:

$$e_0 - e_{mdl} = 6 \cdot \frac{\sqrt{2NA\Delta f}}{k_d} \quad \text{eqn.29}$$

Eqn.29 can be re-written as:

$$e_{mdl} = e_0 - 6 \cdot \frac{\sqrt{2NA\Delta f}}{k_d} \quad \text{eqn.30}$$

Re-writing eqn.23 for $e_{mdl}$ and $B_{mdl}$, we get:

$$A = e_{mdl} \cdot k_d + \frac{\frac{e_{mdl} \cdot k_1}{U} \cdot B_{mdl}}{1 + \frac{e_{mdl} \cdot k_1}{n \cdot U}} \quad \text{eqn.31}$$

Solving eqn.30 and eqn.31 using a mathematical computation program, such as Mathematica, one can obtain plots of $B_{mdl}$ versus different detector parameters.

1.6. Constancy of Analyte Capture Rate Constant '$k_1$'

I have constructed detectors satisfying eqn. 22.1 and found by empirical determination that the response factor curves for different samples (e.g., compounds used in pesticides) are not flat, and appear to meet in a virtual point on the logarithmic analyte concentration axis (x-axis in a plot of the response factors). This indicates that an assumption in eqn.14 that '$k_1$' is constant is not true.

An explanation for the logarithmic decay will now be rendered. Refer to eqn.6 for the following discussion For the sake of argument, assume that 'e' remains constant. For 'k1' to remain constant, doubling the analyte concentration 'B/U' should double the capture rate 'C'. This is valid as long as concentrations 'e/V' and 'B/U' are of the same order of magnitude. When analyte concentration 'B/U' is much larger than free electrons concentration 'eV', doubling 'B/U' increases the possibility of capturing electrons by less than double. Thus '$k_1$' appears to decline as the ratio between analyte concentration and free electron concentration grows higher and higher.

1.7. EC Detector Optimum Design

The foregoing theoretical analysis has been found to agree with the empirical results obtained from a prior art ionization cell having a volume of 1500 microliters, and effective radioactivity of 15 milliCuries. This also explained the cell's nonlinearities, response shifting with contamination levels, baseline noise and MDL.

Furthermore, the theoretical model indicated that an optimum design is achievable. Looking at the MDL plots it is clear that there is a level of effective radioactivity at which the detector is most sensitive. This level is about 1 to 2 milliCurie, depending on analyte $k_1$ and flow rate U. A plot of MDL (cf. FIG. 4) also shows that lower or higher in effective radioactivity causes the MDL becomes higher i.e.; the detector becomes less sensitive.

At the same time, linearity plots show that detectors working in this same effective radio-activity range (1–2 milliCurie), are far more linear than the conventional detectors working at effective radioactivity levels in the range of about 13 milliCuries. In reference to eqn.23, it is clear that making the number of free electrons "$e_0$" sufficiently small to fulfill the condition (e . k1<<n.U) will result in a linear detector working only in the concentration mode. However, the mean free path for $N^{63}$ beta particles is about 1 cm. So, going smaller than 1000 microliters of the ionization cell causes more beta particles to hit the walls and lose their energy with the impact instead of generating more free electrons. As a result less ionization occurs and the effective radioactivity is decreased. Another phenomena occurs with the decreased cell volume; that is more free electrons, recombine with the cell walls. Hence the recombination rate constant $k_d$ becomes larger thus reducing the number of available free electrons.

Figure 2:
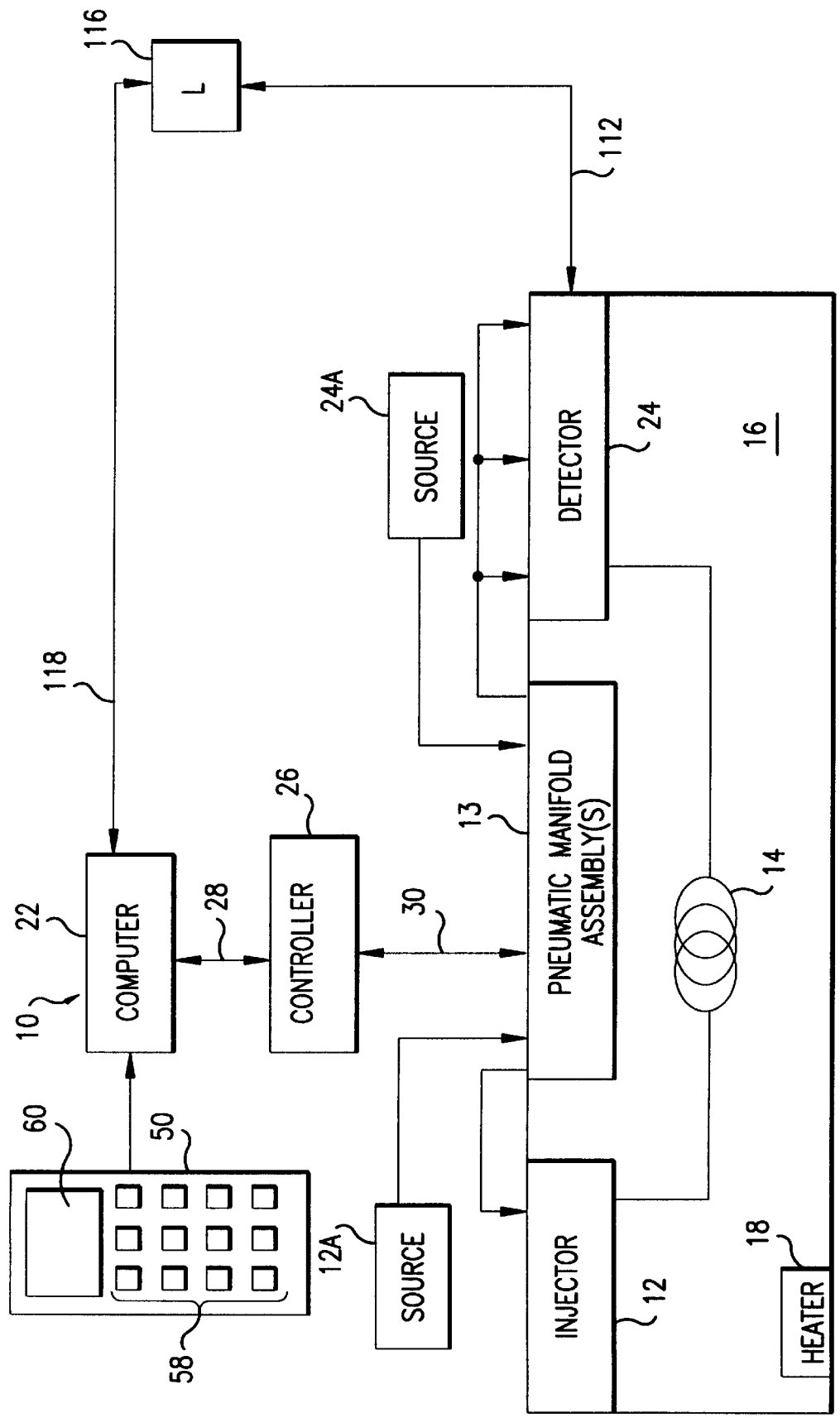
FIG. 2 is simplified schematic representation of a chromatograph constructed according to the present invention.

2.0 Construction and Operation of an Electron Capture Detector in a GC System Accordingly, a novel electron capture detector may be designed for use in an analytical instrument as shown in FIG. 2. The instrument is generally designated chromatograph 10. In the preferred embodiment, the chromatograph 10 is a Hewlett-Packard HP6890 gas chromatograph that is modified to operate a novel electron capture detector constructed according to the teachings herein.

Operation of the chromatograph may be generally understood as follows. In order to perform a chromatographic separation of a given sample compound, a sample is injected with a pressurized carrier gas, by means of an injector 12. The carrier gas supplied to injector 12 is provided from a source 12A through one or more pneumatic manifold assemblies 13, each of which serves in part to control and redirect a plurality of gas flows, including the carrier gas and a plurality of detector gases of appropriate types, such as air, hydrogen, and make-up gas. The detector gases are provided from respective sources (one such source 24A is shown) to the pneumatic manifold assembly 13. Suitable fluid-handling devices such as valves, sensors and the like in the pneumatic manifold assembly 13 are operated under the control of the computer 22 and controller 26 by way of control signals provided on a data and control lines 28, 30. The control and data line 30 also allows the return of sense information from suitable sensors and signal-interface electronics that are provided in the pneumatic manifold assembly 13. Another set of data and control lines 112, 118 allows the return of detector output signal information from linearization and detector output signal interface 116 (hereinafter, interface 116) that are connected to the computer 22 and detector 24, 124.

A column 14 is positioned within an oven 16. The carrier gas/sample combination passing through column 14 is exposed to a temperature profile resulting in part from the operation of a heater 18 within oven 16. During this profile of changing temperatures, the sample will separate into its components primarily due to differences in the interaction of each component with the column 14 at a given temperature. As the components exit column 14 they are detected by an electron capture detector (hereinafter, detector) 24.

Computer 22 maintains overall control of the systems associated with gas chromatograph 10. It will be recognized that any particular gas chromatograph may include more systems than those described in relation to the present invention. For example, an electronic control panel 50 is shown to include an operator interface provided in the form of a keypad 58 and a display 60. It will also be understood that although computer 22 and interface 116 are each shown as a single block, other embodiments are contemplated; for example, the functions of the computer 22 and interface 116 may be subsumed into one unit. The computer 22 includes a central processing unit and all associated peripheral devices, such as random access memories, read-only memories, input/output isolation devices, clocks, and the interface 116 may include a similar central processing unit or, preferably, a digital signal processing unit, and other related electronic components. In the preferred embodiment, the central processor used in computer 22 is a microprocessor. As such, computer 22 and/or interface 116 may include a memory in which information and programming can be stored and retrieved by known methods.

It will be appreciated that the programmed control of the signal processing described hereinbelow with respect to the interface 116 can be implemented by a digital computing means, such as an digital signal processor (dsp) or embedded microprocessor either of which may implement a linearization scheme as described below via firmware, or a dedicated analog network circuit incorporated in a particular detector output signal path within the interface 116. Also, the programming associated with the linearization scheme that is utilized in relation to the present invention will be readily understood to those skilled in the art from the linearization formula to be described below.

Figure 3:
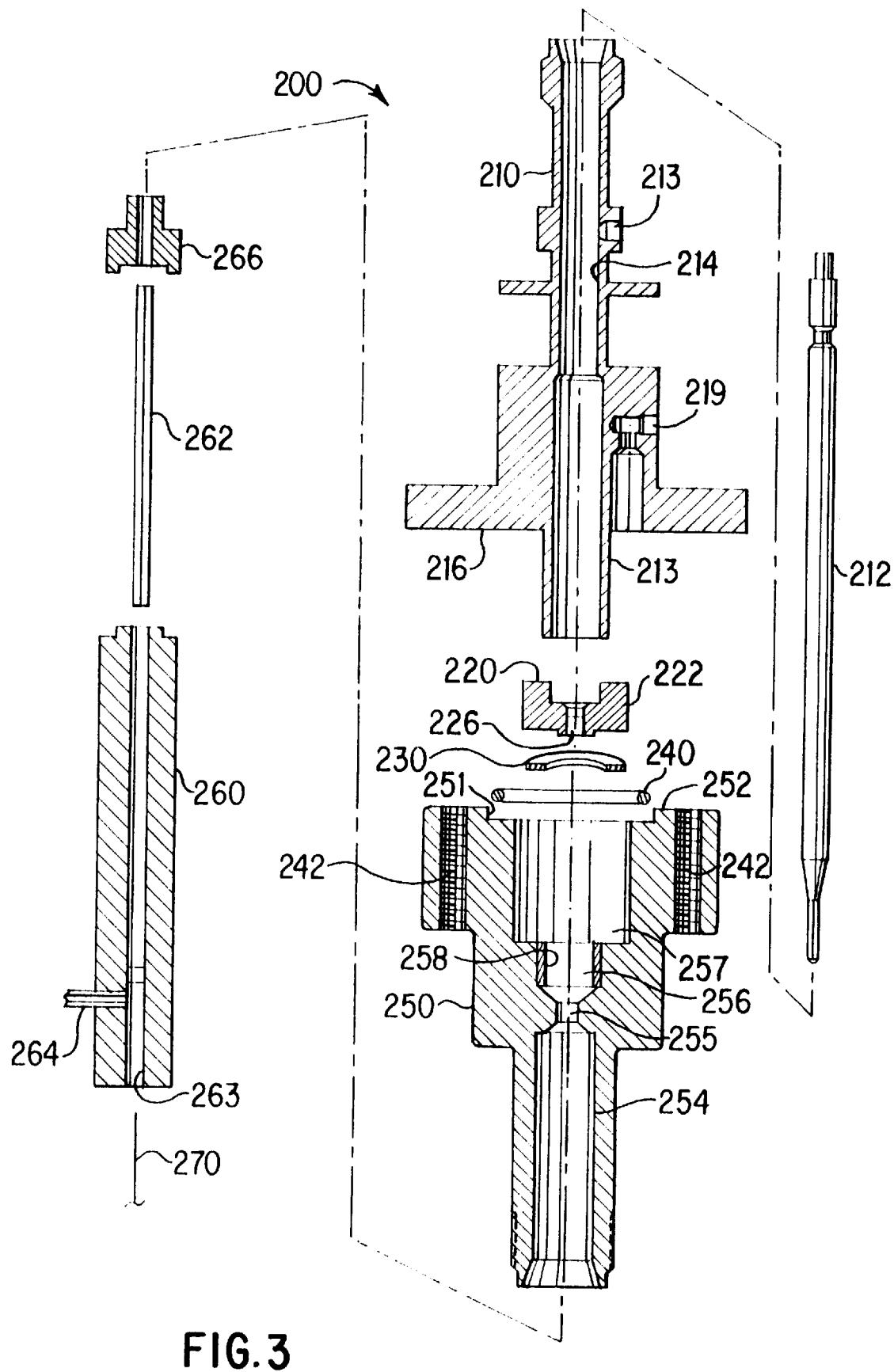
FIG. 3 is an exploded cross-sectional view of an electron capture detector employed in the chromatograph of FIG. 2 and constructed according to the present invention.

As shown in FIG. 3, the preferred embodiment of detector 24 is preferably constructed as a novel electron capture detector 200 especially constructed according to the teachings herein for optimized sensitivity and linearity. The preferred electron capture detector 200 includes an upper body 210, anode 212, flow guide 220, curved washer 230, seal 240, lower body 250, and adapter 260. The upper body 210 is operable as a collector electrode and includes an anode tube 213 that defines a central bore 214 for accommodating the anode 212 in a spaced, concentrically located position therein. The flow guide 220 and an electrically insulating insert (not shown, but typically mounted in the upper end of the central bore 214) are preferably formed of high purity alumina to ensure that the anode 212 is properly positioned and electrically isolated from the upper body 210.

The lower body 250 includes a recess 251 in an interface 252 for receiving the seal 240 and for receiving a corresponding mating surface 216 on the upper body 210. The lower body 250 includes a plurality of coaxially displaced, interconnected interior chambers which are in fluid communication therebetween: a central bore 254, a cap relief 255, an ionization cell 256 having therein a radioactive source 258, and anode chamber 257. The curved washer 230 and flow guide 220 are locatable in the anode chamber 257 such that the uppermost surface of the flow guide 220 is closely fits onto the opposing surface of the anode tube 213. The upper body 210 also includes a purge flow inlet 218 which communicates with the central bore 214 and a purge flow outlet 219 which communicates with the anode chamber 257. Hermetic sealing between the mating surfaces 216, 252 is provided by compression of the seal 240 by appropriate clamping means such as screws extending through screw bores 242 into suitable receiving means (not shown) that may be located on or in the upper body 210. The upper body 210, lower body 250, and certain components therein (such as the curved washer 230) are preferably constructed of inert, heat resistant material such as stainless steel. The adapter 260, upper body 210, and lower body 250 may be heated to a selected temperature by means (not shown) as known in the art.

An outlet end of a chromatographic column 270 is positioned in a liner 262 and the column/liner assembly is located in the central bore 263. Gas to be analyzed, such as the effluent from the chromatographic column 270 is conducted within the column 270. Make-up fluid is thereafter supplied into the central bore 263 and into a central bore of the liner 262 by a make-up gas feed 264. A fluid mixture composed of a substantially uniform mixture of the make-up gas and the column effluent are then passed into the central bore 254 from an adapter cap 266. Thus, when the adapter 260 is fully inserted into the central bore 254, the fluid mixture exits the cap 266 and immediately enters into the ionization cell 256.

The ionization cell 256 has a cup-shaped section with the radioactive source 258 on its side wall being so designed and positioned such that the fluid mixture can pass upwardly into the ionization cell 256 for subsequent ionization of the sample molecules that are present in the fluid mixture. The desired mixing of the effluent and make-up gas is preferably implemented by a mixing device provided in the form of a hollow, tubular liner 262 formed of deactivated quartz and having a flow acceleration region wherein the make-up gas and the effluent are subject to a momentary but substantial increase in velocity, thus causing turbulent flow within the flow acceleration region.

Figure 4:
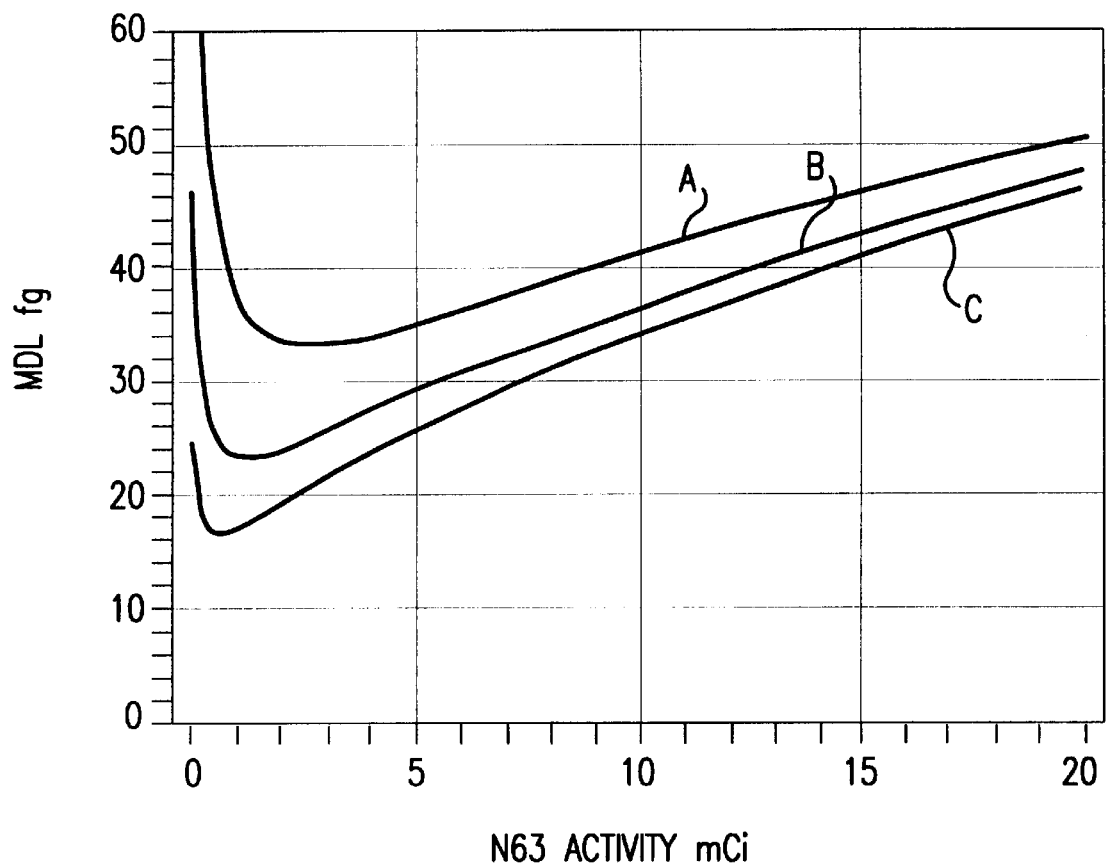
FIG. 4 is a graphical representation of the minimum detectable level (mdl) vs. effective radioactivity calculated and empirically confirmed for a prototype version of the electron capture detector of FIG. 2, showing the preferred optimization of the level of effective radioactivity, according to the present invention.

FIG. 4 is a graphical representation of the minimum detectable level (mdl) vs. effective radioactivity calculated and empirically confirmed for a prototype version of the electron capture detector of FIG. 2, showing the preferred optimization of the level of effective radioactivity, according to the present invention. FIG. 4 illustrates three curves representing the variation in the minimum detectable level ($B_{mdl}$) of a sample with respect to variations in the effective radioactivity. Curves A, B, and C were respectively calculated for flow rates of 35, 70, and 140 milliliters per minute using equation 31 (infra.). These curves were then verified empirically by use of a prototype version of the electron capture detector 200 having ionization cells that were fitted with differing amounts of radioactive source ($Ni_{63}$) so as to exhibit respectively differing levels of effective radioactive in the ionization cell, and operated at the aforementioned total flow rates. Optimization of the minimum detectable level ($B_{mdl}$) and the level of effective radioactivity is seen to be achieved in the range of approximately 0.5 to 4 milliCuries of effective radioactivity, and more preferably in the range of approximately 1–2 milliCuries of effective radioactivity.

Figure 5:
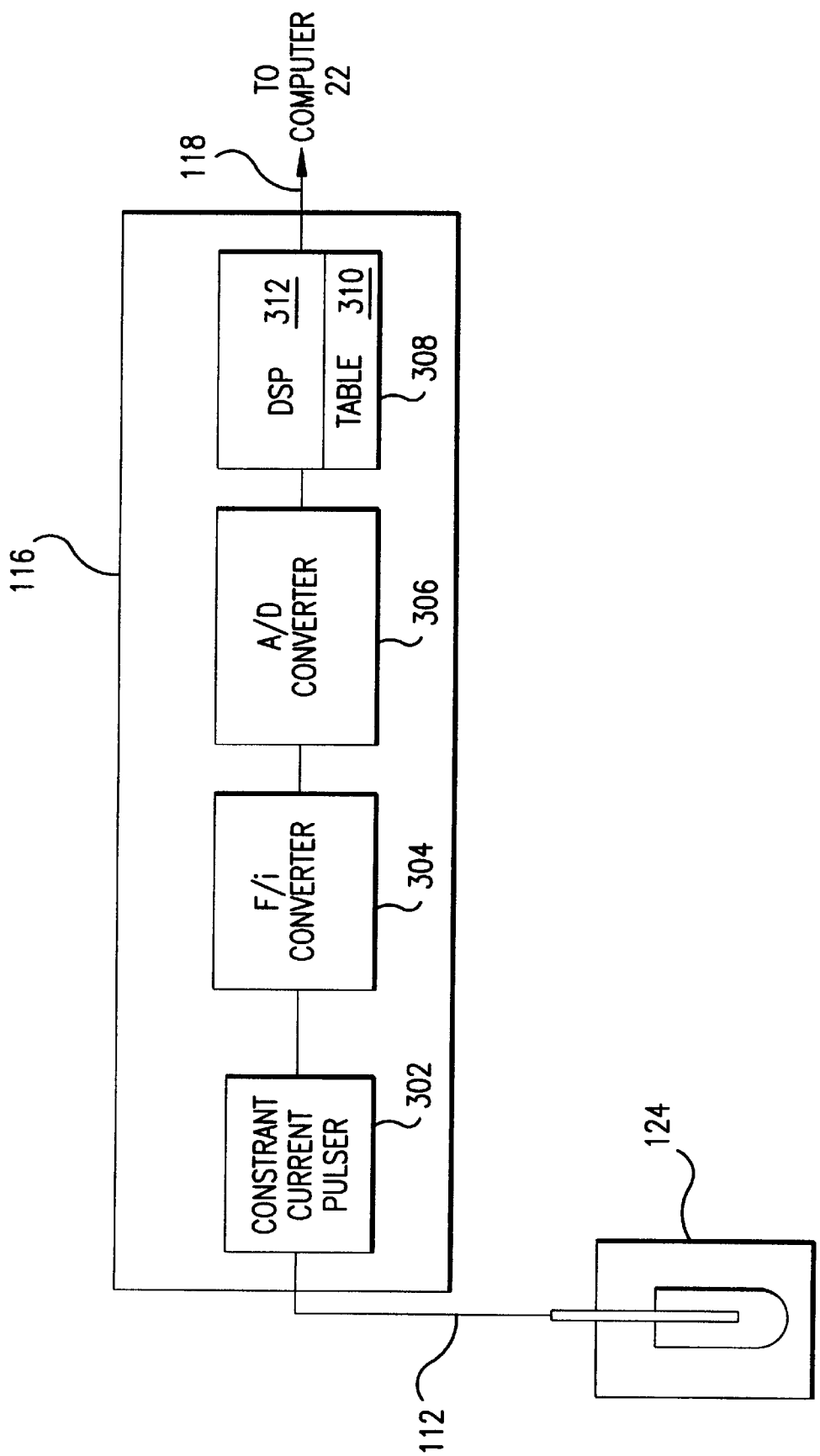
FIG. 5 is a simplified schematic of a detector output signal interface for performing control and signal processing functions in the electron capture detector in FIG. 3.

FIG. 5 is a representation of a preferred embodiment of the interface 116 of FIG. 2. The interface 116 preferably includes a constant current pulse section 302, a frequency-to-current (f/I) converter 304, an analog to digital converter 306, and linearization section 308. Linearization of the response factor is preferably implemented so as to compensate for above-described logarithmic decay of the response factor according to a conversion table 310. Conversion factors in the conversion table 310 are provided according to the following linearizing formula:

$$f_{(lin)} = f[1+(f/f_{(dec)})]^{pwr}$$

Where:

$f_{(lin)}$ = linearized output frequency of the electron capture detector $f$ = non-linearized output frequency of the electron capture detector $f_{(dec)}$ = detector frequency at which $k_1$ begins its observed decline pwr = power of the decline in $k_1$ In a preferred embodiment of the invention, implementation of this linearizing formula was accomplished using firmware operating the conversion table 310 and implemented in a digital signal processor (dsp) 312. Those skilled in the art will understand that this compensation can alternatively be accomplished in discrete electronic circuitry (i.e., in hardware), or via software operating in a microprocessor.

Figure 6A:
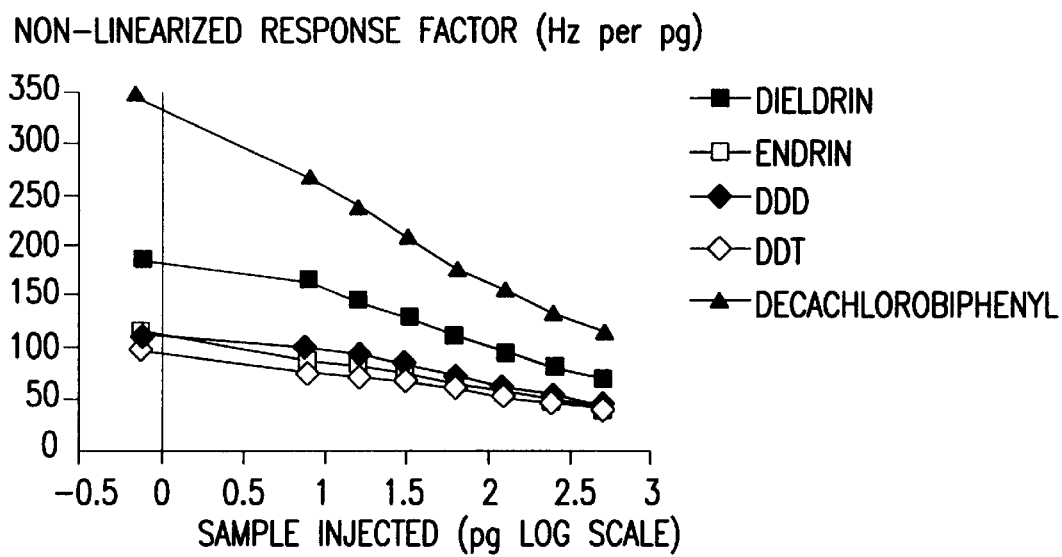
FIGS. 6A and 7A are graphical representations of the nonlinearized response factors vs. injected sample.
Figure 6B:
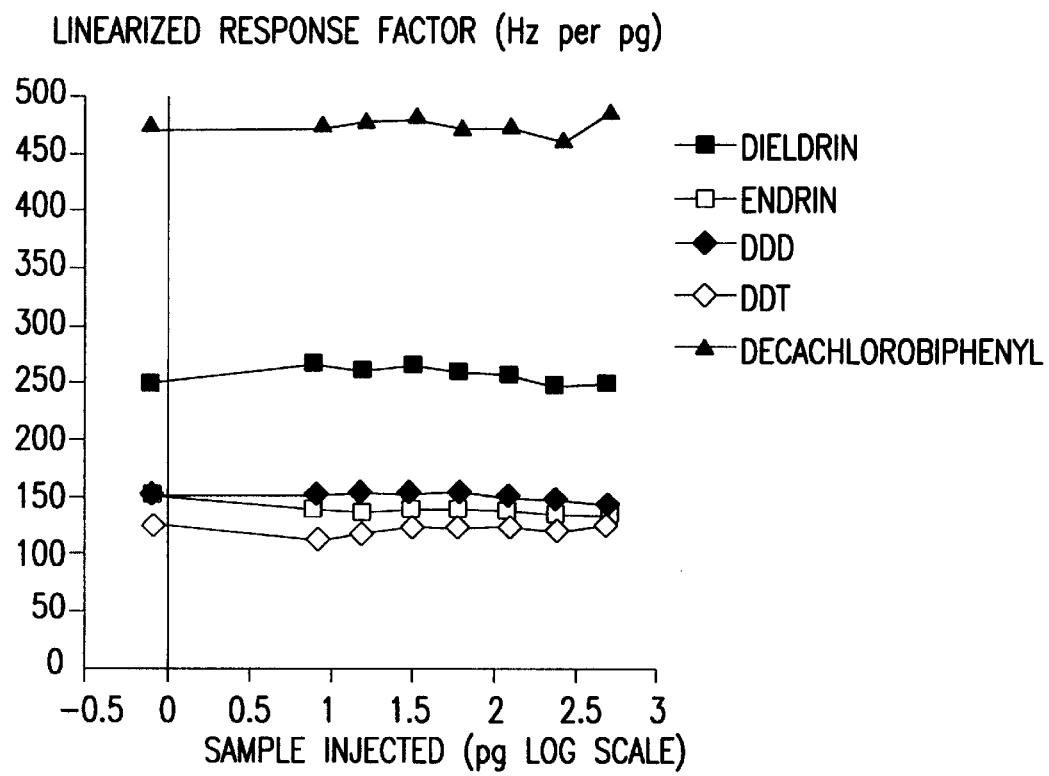
FIGS. 6B and 7B are graphical representations of the linearized response factors vs. injected sample, exhibited by a prototype of the electron capture detector of FIG. 3, showing experimental verification of the operation of the linearization provided in the detector output signal interface of FIG. 5.
Figure 7A:
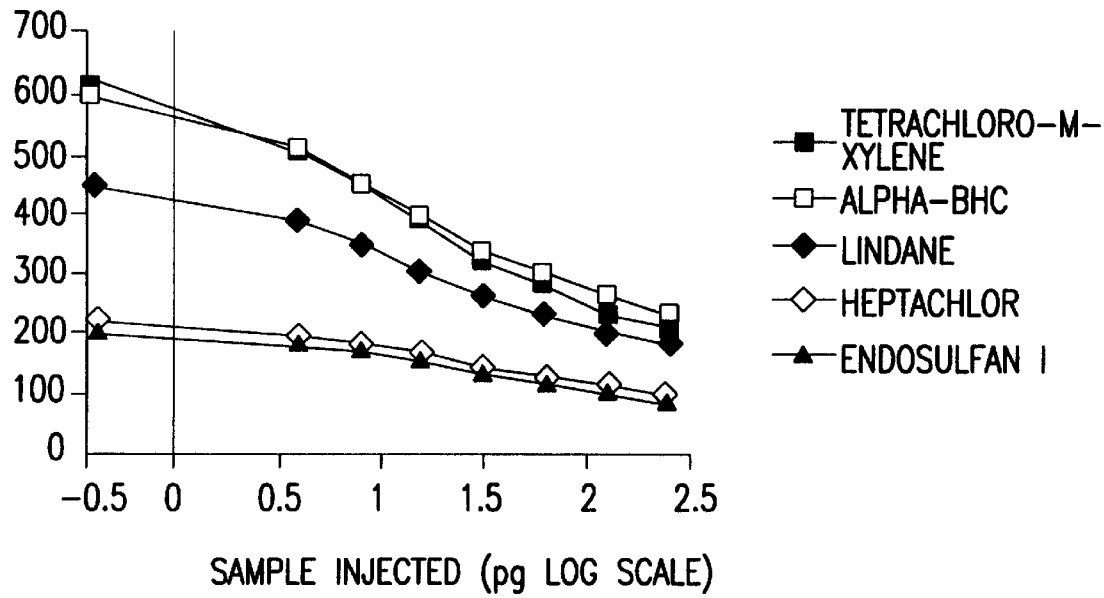
Figure 7B:
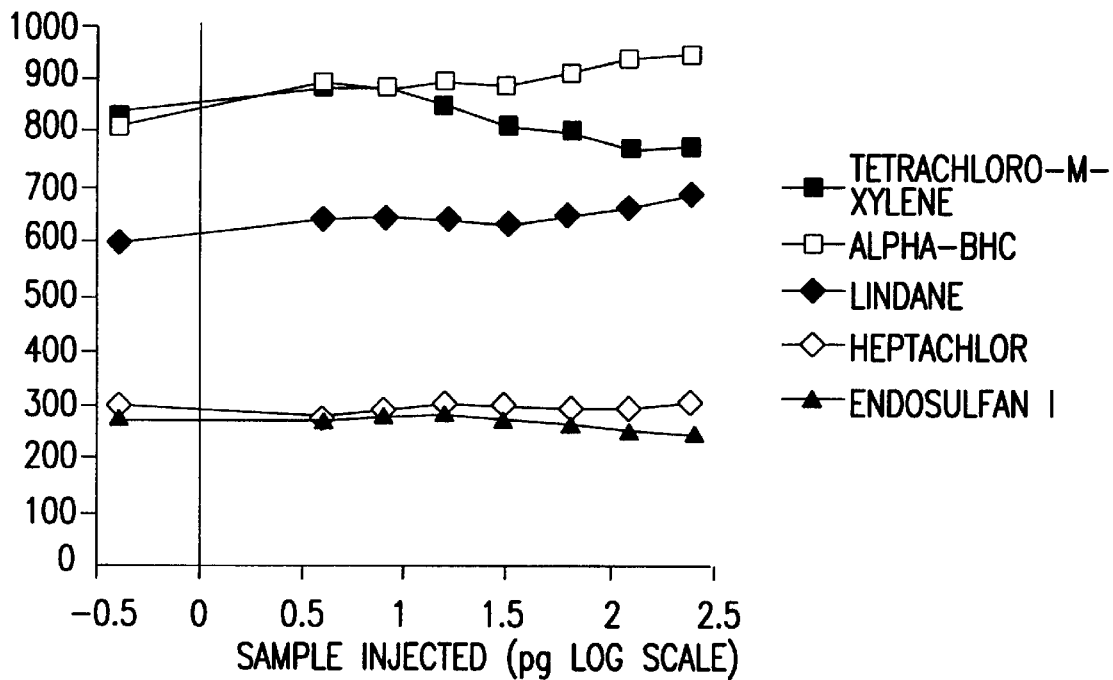

As will be understood by comparison of FIGS. 6A with FIG. 6B, and of FIG. 7A with FIG. 7B, improved quantitative results are represented in the linearized response factors obtained from the electron capture detector 200 illustrated in FIG. 3. In the prototype version of the electron capture detector 200, the ionization cell volume was approximately 150 microliters; the radioactive source was provided in the form of a coating of 7.5 milliCuries of $Ni^{63}$ that was plated on a cylinder fitted to the interior wall of the ionization cell such that the effective radioactivity was approximately 2 milliCuries. The non-linearized response factors shown in FIGS. 6A and 7A were recorded after modification of interface 116 such that the linearization section 308 was inactivated (i.e., bypassed), and thus the detector output response was not subject to linearization. The prototype version of the electron capture detector 100 was then operated with the linearization section 308 being allowed to operate fully according to the teachings herein, and the linearized response factors were recorded in FIGS. 6B and 7B. The benefit of linearization in accordance with the present invention is clearly evident in FIGS. 6B and 7B. The illustrated response curves indicate the improved relationship between an injected sample amount and the resulting peak height in the detector response.

What is claimed is:

1. An electron capture detector for receiving a fluid mixture having an electron-capturing species subject to detection, comprising:

an ionization cell defining an optimum cell volume;

a sample inlet system connected to the ionization cell for providing the fluid mixture in the ionization cell;

a radioactive ionization source associated with said ionization cell volume for generating a plurality of thermal electrons in said fluid mixture in response to an optimum level of effective radioactivity in said ionization cell volume in the range of approximately 1 to 2 milliCuries, whereby the presence of the electron-capturing species in the fluid mixture may react with the thermal electrons to form negative ions; and means located with respect to said cell volume for detecting a subsequent variation in the thermal electron concentration in the fluid mixture.

2. The electron capture detector of claim 1 wherein the optimum cell volume is in the range of 100–150 microliters.

3. An electron capture detector for receiving a fluid mixture having an electron-capturing species subject to detection, comprising:

an ionization cell defining a cell volume;

a radioactive ionization source associated with said ionization cell for generating a plurality of thermal electrons in said fluid mixture, whereby the presence of the electron-capturing species in the fluid mixture may react with the thermal electrons to form negative ions;

signal generating means located with respect to said fluid mixture for detecting a subsequent variation in the thermal electron concentration in the fluid mixture according to a detector response factor and providing a representative signal; and signal compensation means connected to said signal generating means for compensating a logarithmic decline in the detector response factor by altering the signal according to a linearizing formula:

$$f_{(lin)}=f[1+(f/f_{(dec)})]^{pwr}$$

where:

$f_{(lin)}$=linearized output frequency of the electron capture detector $f$=non-linearized output frequency of the electron capture detector $f_{(dec)}$=detector frequency at which $k_1$ begins its observed decline pwr=power of the decline in $k_1$ wherein $K_1$=electron capture rate constant.

4. A method of operating an electron capture detector for receiving a fluid mixture having an electron-capturing species subject to detection according to a detector response factor, comprising the steps of:

providing an ionization cell defining a cell volume;

associating a radioactive ionization source with said ionization cell for generating a plurality of thermal electrons in said fluid mixture, whereby the presence of the electron-capturing species in the fluid mixture may react with the thermal electrons to form negative ions;

generating a signal representing a subsequent variation in the thermal electron concentration in the fluid mixture according to a detector response factor; and altering the signal to compensate for a logarithmic decline in the detector response factor.

5. The method of claim 4, further comprising the step of forcing the ionization cell to operation in a concentration mode.

6. The method of claim 5, wherein the forcing step further comprises the step of forcing the ionization cell to operate according the condition:

$$\frac{e_{mdl} \cdot k_1}{n \cdot U} \ll 1$$

where:

$e_{mdl}$=the value of e (where e=the number of free electrons) when the rate of introduction of the analyte into the ionization cell (molecules $sec^1$) equals the minimum detectable level (MDL), $k_1$=electron capture rate constant, n=the maximum number of electrons that can be captured by one analyte molecule, and U=flow rate.

7. The method of claim 4, wherein the altering step further comprises the step of compensating a logarithmic decline in the response factor by altering the signal derived from the detector response factor according to a linearizing formula:

$$f_{(lin)}=f[1+(f/f_{(dec)})]^{pwr}$$

Where:

$f_{(lin)}$=linearized output frequency of the electron capture detector $f$=non-linearized output frequency of the electron capture detector $f_{(dec)}$=detector frequency at which $k_1$ begins its observed decline pwr=power of the decline in $k_1$ wherein $k_1$=electron capture rate constant.

8. The method of claim 7, wherein the altering step is accomplished via signal processing of the signal according to a compensation factor table.

* * * * *